(12) United States Patent
Zhang et al.

(10) Patent No.: US 8,188,294 B2
(45) Date of Patent: May 29, 2012

(54) PROCESS FOR PREPARING BIPHENYL IMIDAZOLE COMPOUNDS

(75) Inventors: Weijiang Zhang, Concord, CA (US); Pierre-Jean Colson, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 12/891,964

(22) Filed: Sep. 28, 2010

(65) Prior Publication Data

US 2011/0077411 A1  Mar. 31, 2011

Related U.S. Application Data

(60) Provisional application No. 61/246,608, filed on Sep. 29, 2009.

(51) Int. Cl.
*C07D 233/54* (2006.01)
(52) U.S. Cl. .................................. 548/322.5
(58) Field of Classification Search ............ 548/322.5
See application file for complete search history.

(56) References Cited

U.S. PATENT DOCUMENTS

| 5,128,355 A * | 7/1992 | Carini et al. ............ 514/381 |
| 7,915,425 B2 * | 3/2011 | Reddy et al. ............ 548/252 |

| 2008/0269305 A1 | 10/2008 | Allegretti et al. |
| 2009/0023228 A1 | 1/2009 | Allegretti et al. |
| 2010/0081697 A1 | 4/2010 | Chao et al. |

FOREIGN PATENT DOCUMENTS

WO  2010/045420 A1  4/2010

OTHER PUBLICATIONS

International Search Report for International Application No. PCT/2010/050481.

* cited by examiner

*Primary Examiner* — Robert Havlin
(74) *Attorney, Agent, or Firm* — Jeffrey A. Hagenah; Shelley Eberle

(57) ABSTRACT

The invention provides processes for preparing intermediates useful for preparing compounds of the formula:

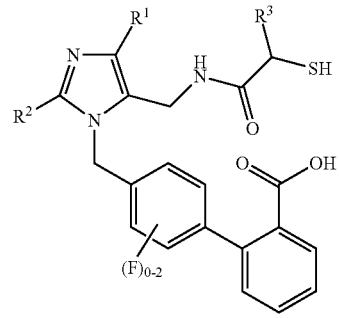

or a salt thereof, where $R^{1-3}$ are as defined in the specification.

5 Claims, 4 Drawing Sheets

PROCESS FOR PREPARING BIPHENYL IMIDAZOLE COMPOUNDS

CROSS-REFERENCE TO RELATED APPLICATIONS

This application claims the benefit of U.S. Provisional Application No. 61/246,608, filed on Sep. 29, 2009; the entire disclosure of which is incorporated herein by reference.

BACKGROUND OF THE INVENTION

1. Field of the Invention

The present invention relates to processes and intermediates for preparing biphenyl imidazole compounds that are useful in preparing compounds having angiotensin II type 1 receptor antagonist activity and neprilysin-inhibition activity.

2. State of the Art

Commonly-assigned U.S. Publication Nos. 2008/0269305 and 2009/0023228, both to Allegretti et al. filed on Apr. 23, 2008, disclose novel compounds that possess $AT_1$ receptor antagonist activity and neprilysin (NEP) enzyme inhibition activity, the disclosures of which are incorporated herein by reference. In one embodiment, these applications disclose novel compounds such as 4'-{2-ethoxy-4-ethyl-5-[((S)-2-mercapto-4-methylpentanoylamino)methyl]imidazol-1-yl-methyl}-3'-fluorobiphenyl-2-carboxylic acid.

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point, which allows the material to be processed without significant decomposition. A crystalline freebase form of 4'-{2-ethoxy-4-ethyl-5-[((S)-2-mercapto-4-methylpentanoylamino)-methyl]imidazol-1-ylmethyl}-3'-fluorobiphenyl-2-carboxylic acid is disclosed in commonly-assigned U.S. Publication No. 2010/0081697, to Chao et al. filed on Sep. 29, 2009, the disclosure of which is incorporated herein by reference.

The compounds disclosed in these publications and applications are prepared by techniques that typically require that one or more biphenyl imidazole intermediates are purified by chromatography. There are several advantages to developing processes where such purification steps are not necessary. This invention addresses that need.

SUMMARY OF THE INVENTION

The present invention relates to novel intermediates and improved processes for preparing intermediates useful for preparing compounds of formula IV:

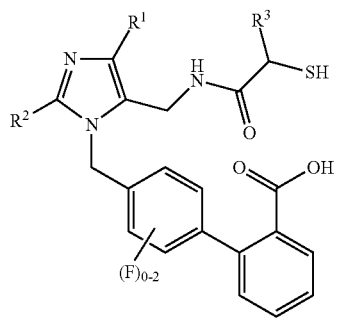

(IV)

or a salt thereof, where $R^1$ is —$C_{1-6}$alkyl; $R^2$ is —O—$C_{1-5}$alkyl; and $R^3$ is —$C_{1-6}$alkyl, —$C_{0-3}$alkylenearyl, —$C_{0-3}$alkyleneheteroaryl, or —$C_{0-3}$alkylene-$C_{3-7}$cycloalkyl. In one particular embodiment, the invention relates to processes for preparing intermediates useful for preparing 4'-{2-ethoxy-4-ethyl-5-[((S)-2-mercapto-4-methylpentanoylamino)methyl]imidazol-1-ylmethyl}-3'-fluorobiphenyl-2-carboxylic acid.

One aspect of the invention relates to a process for preparing a compound of formula I:

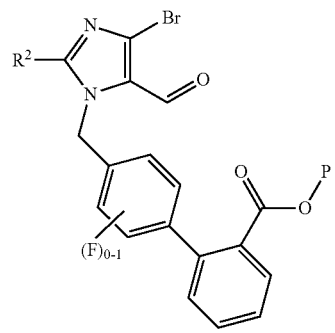

(I)

where $R^2$ is —O—$C_{1-5}$alkyl; and P is a carboxylic acid protecting group; the process comprising the step of reacting a compound of formula 1:

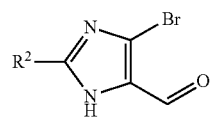

(1)

with a compound of formula 2:

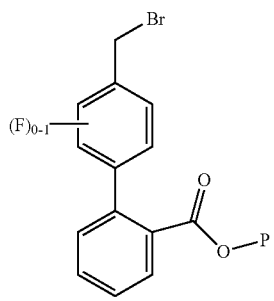

(2)

in an organic diluent and a basic aqueous diluent in the presence of a phase transfer catalyst, where the diluents are substantially immiscible, to form a compound of formula I.

In one embodiment, this process further comprises the step of preparing a crystalline form of the compound of formula I. One aspect of the invention relates to crystalline 4'-(4-bromo-2-ethoxy-5-formylimidazol-1-ylmethyl)-3'-fluorobiphenyl-2-carboxylic acid tert-butyl ester.

Another aspect of the invention relates to a process for preparing a compound of formula II:

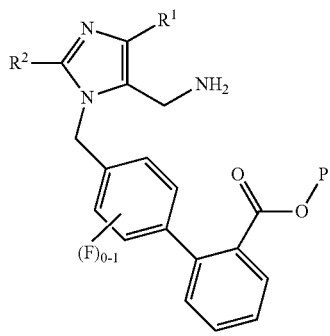

(II)

or a salt thereof; where $R^1$ is —$C_{1-6}$ alkyl; $R^2$ is —O—$C_{1-5}$ alkyl; and P is a carboxylic acid protecting group; the process comprising the steps of:

(a) reacting a compound of formula I:

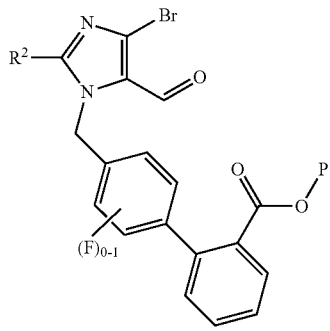

(I)

with a potassium-$C_{1-6}$alkyl-trifluoroborate reagent in the presence of a palladium-phosphine catalyst to form a compound of formula 3:

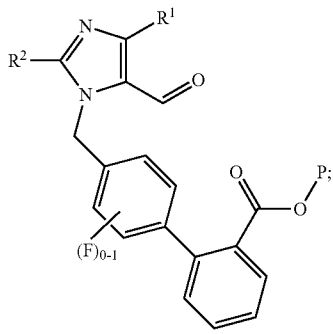

(3)

(b) reacting the compound of formula 3 with hydroxylamine or a salt thereof to form a compound of formula 4:

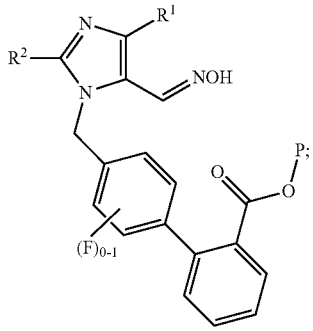

(4)

and (c) reacting the compound of formula 4 with a reducing agent to form a compound of formula II or a salt thereof.

In one embodiment, this process further comprises the step of preparing a crystalline form of the compound of formula II. One aspect of the invention relates to crystalline 4'-(5-aminomethyl-2-ethoxy-4-ethylimidazol-1-ylmethyl)-3'-fluoro-biphenyl-2-carboxylic acid t-butyl ester.

Yet another aspect of the invention relates to a process for preparing a compound of formula III:

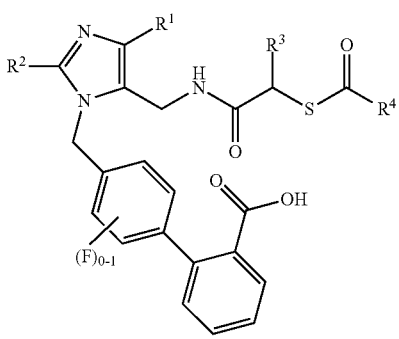

(III)

or a salt thereof where $R^1$ is —$C_{1-6}$alkyl; $R^2$ is —O—$C_{1-5}$ alkyl; $R^3$ is —$C_{1-6}$alkyl, —$C_{0-3}$alkylenearyl, —$C_{0-3}$alkyleneheteroaryl, or —$C_{0-3}$alkylene-$C_{3-7}$cycloalkyl; and $R^4$ is —$C_{1-6}$alkyl, —$C_{0-6}$alkylene-$C_{3-7}$cycloalkyl, —$C_{0-6}$alkylenearyl, or —$C_{0-6}$alkylenemorpholine; the process comprising the steps of:

(a) reacting a compound of formula I:

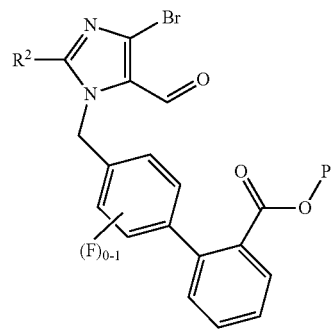

(I)

with a potassium-$C_{1-6}$alkyl-trifluoroborate reagent in the presence of a palladium-phosphine catalyst to form a compound of formula 3:

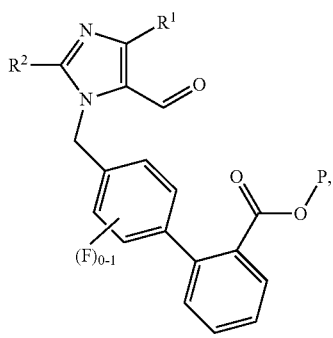

(3)

where P is a carboxylic acid protecting group;

(b) reacting the compound of formula 3 with hydroxylamine or a salt thereof to form a compound of formula 4:

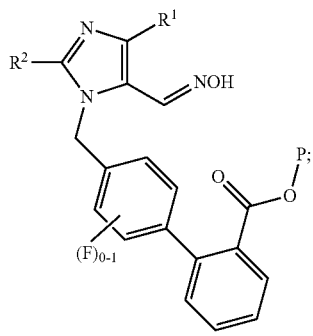

(4)

(c) reacting the compound of formula 4 with a reducing agent to form a compound of formula II or a salt thereof.

(d) reacting the compound of formula II or a salt thereof with a compound of formula 5:

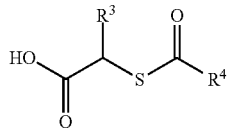
(5)

or a salt thereof, in the presence of an amine-carboxylic acid coupling reagent to form a compound of formula 6:

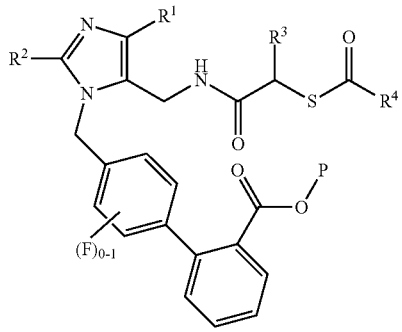
(6)

or a salt thereof; and (e) removing the carboxylic acid protecting group, P, from the compound of formula 5 or a salt thereof, to form a compound of formula III or a salt thereof.

In one embodiment, this process further comprises the step of preparing a crystalline form of the compound of formula III. One aspect of the invention relates to crystalline 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid.

Another aspect of the invention relates to a novel intermediates used in the processes of the invention. In one such aspect of the invention novel intermediates have formula 3 or 4.

BRIEF DESCRIPTION OF THE DRAWINGS

Various aspects of the present invention are illustrated by reference to the accompanying drawings.

DETAILED DESCRIPTION OF THE INVENTION

Figure 1:
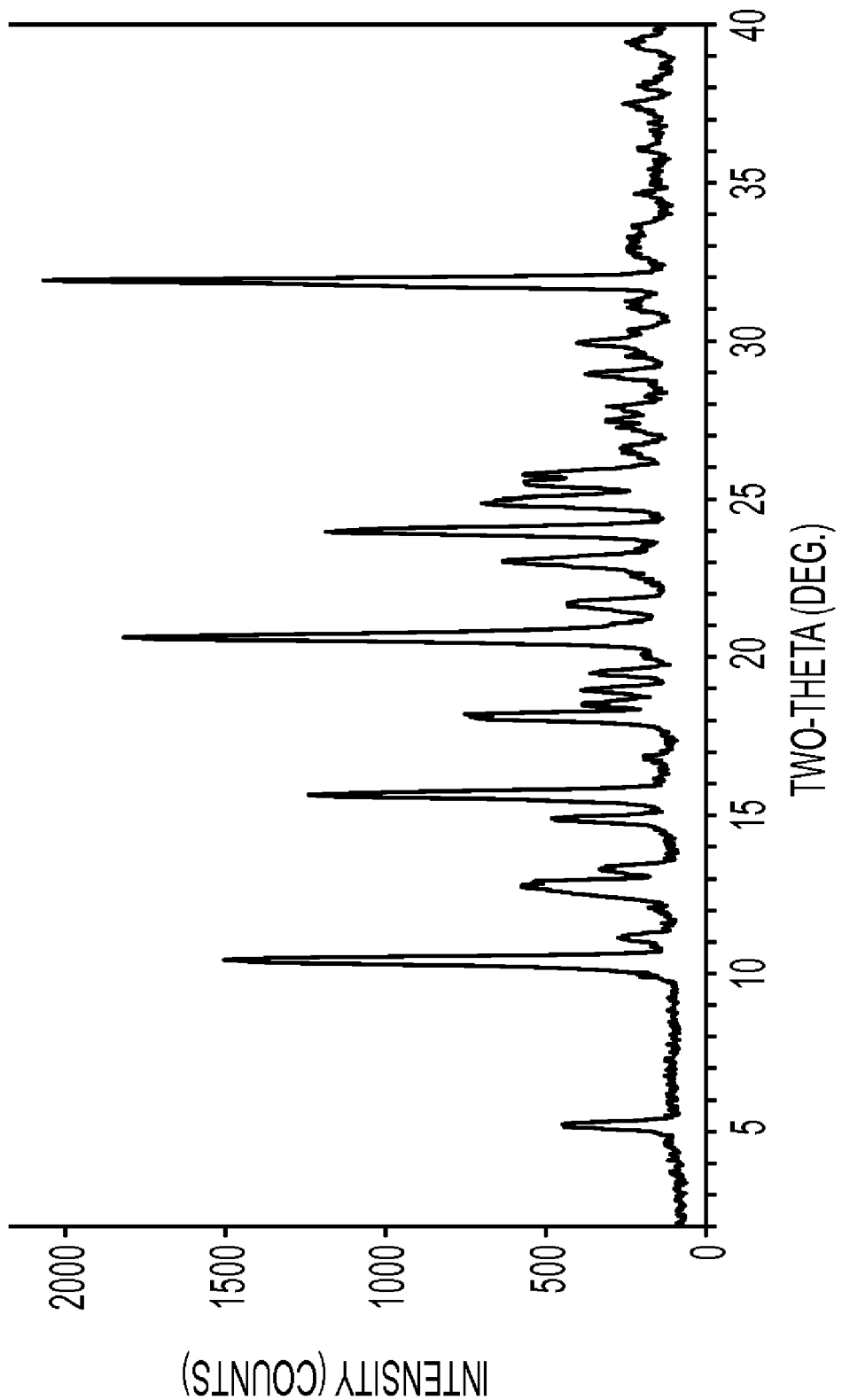
FIG. 1 shows a powder x-ray diffraction (PXRD) pattern of the crystalline form of 4'-(5-aminomethyl-2-ethoxy-4-ethylimidazol-1-ylmethyl)-3'-fluorobiphenyl-2-carboxylic acid t-butyl ester (formula IIa).

The invention relates to novel processes for preparing compounds of formula I:

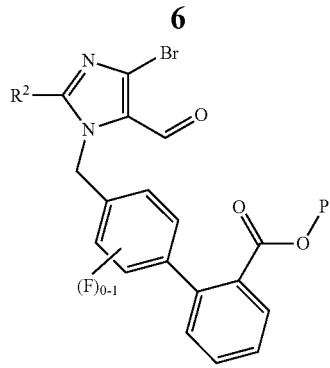
(I)

and compounds of formula II:

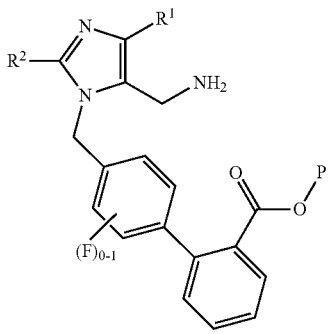
(II)

and compounds of formula III:

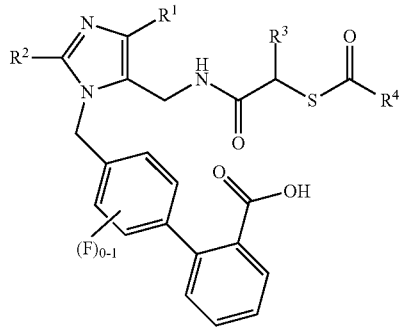
(III)

or a salt thereof.

The $R^1$ moiety is —$C_{1-6}$alkyl, examples of which include —$CH_3$ and —$CH_2CH_3$. In one particular embodiment, $R^1$ is —$CH_2CH_3$.

The $R^2$ moiety is —O—$C_{1-5}$alkyl, examples of which include —$OCH_3$, —$OCH_2CH_3$, —$OCH(CH_3)_2$, —$O(CH_2)_2CH_3$, —$O(CH_2)_3CH_3$, and —$OCH_2CH(CH_3)_2$. In one particular embodiment, $R^2$ is —O—$CH_2CH_3$.

The $R^3$ moiety is selected from —$C_{1-6}$alkyl, —$C_{0-3}$alkylenearyl, —$C_{0-3}$alkyleneheteroaryl, and —$C_{0-3}$alkylene-$C_{3-7}$cycloalkyl. Examples of —$C_{1-6}$alkyl include —$CH_3$, —$CH_2CH_3$, —$CH(CH_3)_2$, —$(CH_2)_2CH_3$, —$(CH_2)_3CH_3$, —$CH(CH_3)CH_2CH_3$, —$CH_2CH(CH_3)_2$, —$CH_2C(CH_3)_3$, —$(CH_2)_2CH(CH_3)_2$, and —$(CH_2)_4CH_3$. In one particular embodiment, $R^3$ is —$CH_2CH(CH_3)_2$. Examples of —$C_{0-3}$alkylenearyl include phenyl, benzyl, —$CH_2$-biphenyl, —$(CH_2)_2$-phenyl and —$CH_2$-naphthalen-1-yl. Examples of —$C_{0-3}$alkyleneheteroaryl include —$CH_2$-pyridyl, —$CH_2$-furanyl, —$CH_2$-thienyl, and —$CH_2$-thiophenyl. Examples of —$C_{0-3}$alkylene-$C_{3-7}$cycloalkyl include —$CH_2$-cyclopropyl, cyclopentyl, —$CH_2$-cyclopentyl, -cyclohexyl, and —$CH_2$-cyclohexyl.

The $R^4$ moiety is selected from —$C_{1-6}$alkyl, —$C_{0-6}$alkylene-$C_{3-7}$cycloalkyl, —$C_{0-6}$alkylenearyl, and —$C_{0-6}$alkylenemorpholine. Examples of —$C_{1-6}$alkyl include —$CH_3$, —$CH_2CH_3$, —$CH(CH_3)_2$, —$C(CH_3)_3$, and —$CH_2CH(CH_3)_2$. In one particular embodiment, $R^4$ is —$CH_3$. Examples of —$C_{0-6}$alkylene-$C_{3-7}$cycloalkyl include -cyclopentyl, -cyclohexyl, and —$CH_2$-cyclopentyl. Examples of —$C_{0-6}$alkylenearyl include phenyl. Examples of —$C_{0-6}$alkylenemorpholine include —$CH_2$-morpholine and —$(CH_2)_2$-morpholine.

The P moiety is a "carboxylic acid protecting group", a term used herein to mean a group covalently attached to a carboxyl functional group that prevents the functional group from undergoing undesired reactions but which permits the functional group to be regenerated (i.e., deprotected or unblocked) upon treatment of the protecting group with a suitable reagent. Representative carboxylic acid protecting groups include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl(benzhydryl, DPM), and the like. In one particular embodiment, P is t-butyl. Other representative carboxylic acid protecting group are described, for example, in T. W. Greene and G. M. Wuts, *Protecting Groups in Organic Synthesis*, Third Edition, Wiley, New York, 1999.

DEFINITIONS

When describing the compounds and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The compounds described herein have typically been named using the AutoNom feature of the commercially-available MDL® ISIS/Draw software (Symyx, Santa Clara, Calif.).

As used herein, the phrase "having the formula" or "having the structure" is not intended to be limiting and is used in the same way that the term "comprising" is commonly used.

The term "alkyl" means a monovalent saturated hydrocarbon group which may be linear or branched. Unless otherwise defined, such alkyl groups typically contain from 1 to 10 carbon atoms and include, for example, —$C_{1-5}$alkyl and —$C_{1-6}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl, and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "$C_{3-7}$cycloalkyl" means a cycloalkyl group having from 3 to 7 carbon atoms, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —$C_{0-3}$alkylene- and —$C_{0-6}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl, and the like. It is understood that when the alkylene term include zero carbons such as —$C_{0-3}$alkylene-, such terms are intended to include a single bond.

The term "aryl" means a monovalent aromatic hydrocarbon having a single ring (for example, phenyl) or fused rings. Fused ring systems include those that are fully unsaturated (for example, naphthalene) as well as those that are partially unsaturated (for example, 1,2,3,4-tetrahydronaphthalene). Unless otherwise defined, such aryl groups typically contain from 6 to 10 carbon ring atoms and include, for example, —$C_{6-10}$aryl. Representative aryl groups include, by way of example, phenyl and naphthalene-1-yl, naphthalene-2-yl, and the like.

The term "cycloalkyl" means a monovalent saturated carbocyclic hydrocarbon group. Unless otherwise defined, such cycloalkyl groups typically contain from 3 to 10 carbon atoms and include, for example, —$C_{3-6}$cycloalkyl and —$C_{3-7}$cycloalkyl. Representative cycloalkyl groups include, by way of example, cyclopropyl, cyclobutyl, cyclopentyl, cyclohexyl, and the like.

The term "heteroaryl" means a monovalent aromatic group having a single ring or two fused rings and containing in the ring(s) at least one heteroatom (typically 1 to 3) selected from nitrogen, oxygen and sulfur. Unless otherwise defined, such heteroaryl groups typically contain from 5 to 10 total ring atoms and include, for example, —$C_{2-9}$heteroaryl. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzoimidazole, benzthiazole, quinoline, isoquinoline, quinazoline, quinoxaline, and the like, where the point of attachment is at any available carbon or nitrogen ring atom.

The term "melting point" as used herein means the temperature at which the maximum endothermic heat flow is observed by differential scanning calorimetry, for the thermal transition that corresponds to the solid-to-liquid phase change.

The term "salt" when used in conjunction with a compound means a salt of the compound derived from an inorganic or organic base or from an inorganic or organic acid. Salts derived from inorganic bases include aluminum, ammonium, calcium, copper, ferric, ferrous, lithium, magnesium, manganic, manganous, potassium, sodium, zinc, and the like. Particularly preferred are ammonium, calcium, magnesium, potassium and sodium salts. Salts derived from organic bases include salts of primary, secondary and tertiary amines, including substituted amines, cyclic amines, naturally-occurring amines, and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic, and the like. Particularly preferred are citric, hydrobromic, hydrochloric, maleic, phosphoric, sulfuric and tartaric acids. In addition, when a compound of contains both a basic moiety, such as an amine or imidazole, and an acidic moiety such as a carboxylic acid, zwitterions may be formed and are included within the term "salt" as used herein. The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient.

Process Conditions

Suitable inert diluents for use in the process of the invention include, by way of illustration and not limitation, organic diluents such as acetic acid, tetrahydrofuran (THF), acetonitrile (MeCN), N,N-dimethylformamide (DMF), N,N-dimethylacetamide, N-methylpyrrolidinone, dimethyl sulfoxide (DMSO), toluene, dichloromethane (DCM), acetone, ethyl acetate, isopropyl acetate, methyl t-butyl ether, chloroform ($CHCl_3$), carbon tetrachloride ($CCl_4$), 1,4-dioxane, methanol, ethanol, propanol, isopropanol, butanol, ethylene glycol, and the like. Aqueous diluents may also be used, and include water as well as basic and acidic aqueous diluents. Combinations of any of the foregoing diluents are also contemplated.

Suitable polar, protic solvents for use in the process of the invention include, by way of illustration and not limitation, methanol, ethanol, propanol, isopropanol, butanol, ethylene glycol, water, acetic acid, and the like.

There are numerous bases that are suitable for use in the process of the invention. Exemplary organic bases include, by way of illustration and not limitation: amines including primary alkylamines (e.g., methylamine, ethanolamine, the buffering agent tris, and the like), secondary alkylamines (e.g., dimethylamine, methylethanolamine, N,N-diisopropylethylamine (DIPEA), and the like), tertiary amines (e.g., trimethylamine, triethylamine, and the like); ammonia compounds such as ammonium hydroxide and hydrazine; alkali metal hydroxides such as sodium hydroxide, sodium methoxide, potassium hydroxide, potassium t-butoxide, and the like; metal hydrides; and alkali metal carboxylate salts such as sodium acetate and the like). Exemplary inorganic bases, include, by way of illustration and not limitation: alkali metal carbonates such as lithium carbonate, potassium carbonate, cesium carbonate, sodium carbonate, sodium bicarbonate, and the like; other carbonates such as calcium carbonate and the like; and alkali metal phosphates such as potassium phosphate and the like).

There are numerous acids that are suitable for use in the process of the invention, and include, by way of illustration and not limitation, boric, carbonic, nitric ($HNO_3$), phosphoric ($H_3PO_4$), sulfamic and sulfuric ($H_2SO_4$) acids, as well as hydrohalic acids such as hydrobromic (HBr), hydrochloric (HCl), hydrofluoric (HF), and hydroiodic (HI) acid.

Upon completion of any of the process steps, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, HCl); washing (for example, with ethanol, heptanes, saturated aqueous NaCl, saturated $NaHCO_3$, $Na_2CO_3$ (5%), $CHCl_3$ or 1M NaOH); distillation; drying (for example, over $MgSO_4$, over $Na_2SO_4$, under nitrogen, or under reduced pressure); precipitation; filtration; crystallizing (for example, from ethanol, heptanes or isopropyl acetate); and/or being concentrated (for example, in vacuo).

Upon completion of any of the crystallization steps, the crystalline compound can be isolated from the reaction mixture by any conventional means such as precipitation, concentration, centrifugation, drying (for example, at room temperature), and the like.

The process for preparing a compound of formula I is a one step alkylation reaction, which involves combining an imidazole compound of formula 1 with a biphenyl compound of formula 2 to form a compound of formula I. Compounds of formula 1 and 2 can be prepared by conventional procedures using commercially available starting materials and conventional reagents. For example, see the Preparations described herein as well as U.S. Publication Nos. 2008/0269305 and 2009/0023228, both to Allegretti et al.

In one embodiment, a slight excess of the imidazole compound of formula 1 is used based on the amount of the biphenyl compound of formula 2. In one embodiment, from about 1 to about 2 equivalents of the imidazole are used, and in another embodiment, about 1 to 1.5 equivalents are used.

Typically, the compounds of formula 1 and 2 are combined in an organic diluent and a basic aqueous diluent in the presence of a phase transfer catalyst. In one embodiment, a slight excess of the basic aqueous diluent is used based on the amount of the imidazole compound of formula 1. In one embodiment, from about 1 to about 2 equivalents of the basic aqueous diluent are used, and in another embodiment, about 1 to 1.5 equivalents are used.

Exemplary phase transfer catalysts include quaternary ammonium salts such as tetrabutylammonium bromide ($Bu_4NBr$), didecyldimethylammonium bromide (DDAB), methyltriphenylphosphonium bromide, methyltridecylammonium chloride, and the like; and in one embodiment is tetrabutylammonium bromide. In one embodiment, from about 0.01 to about 1.0 equivalents of a phase transfer catalyst are used based on the amount of the biphenyl compound of formula 2; and in another embodiment, about 0.03 to about 0.07 equivalents are used.

The organic diluent and the basic aqueous diluent are substantially immiscible, which means that the two diluents do not mix to form a solution, i.e., they are substantially insoluble in each other and usually exist in separate phases when mixed; noting, however, that there could potentially be a small amount of mixing between the two diluents at their interface. In one embodiment the organic diluent is toluene and the basic aqueous diluent is NaOH.

Formation of the compound of formula I is typically conducted at a temperature ranging from about 20° C. to about 40° C.; and in one embodiment at a temperature ranging from about 25° C. to about 35° C. for about 24 to about 72 hours, and in one embodiment for about 48 to 60 hours, or until formation of the compound of formula I is substantially complete.

When formation of the compound of formula I is substantially complete, the resulting product is then isolated and purified by conventional procedures. The compound of formula I is optionally crystallized by treatment with ethanol to complete dissolution, cooling to effect crystallization, and isolating the resulting solids to yield the crystalline material. Typically dissolution is conducted at a temperature ranging from about 40° C. to about 70° C., and in one embodiment at a temperature ranging from about 50° C. to 60° C. The cooling step is done at a temperature ranging from about 0° C. to about 10° C., and in one embodiment at a temperature ranging from about 2° C. to 6° C., for about 2 to 6 hours, or until formation of crystals. Upon completion of the crystallization step, the crystalline compound of formula I can be isolated from the reaction mixture by any conventional means.

Previous methods of preparing compounds of formula I often resulted in obtaining a high percentage of formula 1 by-products, often as high as 15%. Use of an organic diluent and a basic aqueous diluent, in combination with a phase transfer catalyst, as in the present method, has reduced the amount of by-product to less than 2%, providing a reaction with better selectivity than in prior methods.

The process for preparing a compound of formula II or a salt thereof is conducted in three steps. The first step of the process is a Suzuki coupling reaction, which involves combining one equivalent of an aldehyde of formula I with one or more equivalents of a potassium-$C_{1-6}$alkyl-trifluoroborate reagent in the presence of a palladium-phosphine catalyst to form a compound of formula 3.

Aldehydes of formula I used in the process of the invention can be made by the methods described herein or can be prepared by conventional procedures using commercially available starting materials and conventional reagents. For example, see the Preparations described herein as well as U.S. Publication Nos. 2008/0269305 and 2009/0023228, both to Allegretti et al., which describes various methods for preparing such compounds.

Typically, the aldehyde of formula I and the potassium-$C_{1-6}$ alkyl-trifluoroborate reagent are combined with the palladium-phosphine catalyst in an inert diluent in the presence of an excess amount of a suitable base to form a reaction mixture. In one embodiment, from about 1 to about 2 equivalents of the potassium-$C_{1-6}$alkyl-trifluoroborate reagent are used based on the amount of aldehyde; and in another embodiment, about 1.4 to about 1.5 equivalents are used.

The potassium-$C_{1-6}$alkyl-trifluoroborate reagent is selected based upon the desired $R^1$ group. For example, to prepare a compound of formula 3 where $R^1$ is ethyl, a suitable potassium-$C_{1-6}$alkyl-trifluoroborate reagent is potassium ethyl trifluoroborate.

The palladium-phosphine catalyst may be a single catalyst containing palladium and phosphine, such as bis(triphenylphosphine)palladium(II), tetrakis(triphenylphosphine)-palladium(0) (Pd(PPh$_3$)$_4$), [1,1'-bis(diphenylphosphino)-ferrocene]dichloropalladium(II), bis[1,2-bis(diphenylphosphino)propane]palladium(0), and the like. Alternately, the palladium-phosphine catalyst may be a combination of a palladium catalyst and a source of phosphine. Exemplary palladium catalysts include palladium(II)acetate (Pd(OAc)$_2$), palladium(II)chloride (PdCl$_2$), and the like. Suitable sources of phosphine include di(1-adamantyl)-n-butylphosphine, triphenylphosphine, ethyldiphenylphosphine, dicyclohexyl-phenylphosphine, 2-pyridyldiphenylphosphine, bis(6-methyl-2pyridyl)phenylphosphine, tri-p-chlorophenylphosphine, tri-pmethoxyphenylphosphine, and the like. In one embodiment, the palladium catalyst is palladium(II)acetate and the source of phosphine is di(1-adamantyl)-n-butylphosphine.

In one embodiment, from about 0.01 to about 0.04 equivalents of a palladium catalyst and about 0.02 to about 0.06 equivalents of a phosphine source are used based on the amount of aldehyde; and in another embodiment, about 0.02 to about 0.03 equivalents of a palladium catalyst and about 0.03 to about 0.05 equivalents of a phosphine source are used. In another embodiment, from about 0.03 to about 0.1 equivalents of a palladium-phosphine catalyst is used based on the amount of aldehyde; and in another embodiment, about 0.05 to about 0.08 equivalents are used.

An excess amount of base is used, typically from about 3.0 to about 6.0 equivalents based on the amount of aldehyde, and in one embodiment, about 3.0 to about 4.0 equivalents. In one embodiment, the inert diluent is a mixture of toluene and water. In another embodiment the base is an alkali metal carbonate such as cesium carbonate.

Formation of the compound of formula 3 is typically conducted at a temperature ranging from about 80° C. to about 100° C.; and in one embodiment at a temperature ranging from about 85° C. to about 95° C. for about 12 to about 20 hours, and in one embodiment for about 14 to 18 hours, or until formation of the compound of formula 3 is substantially complete. When formation of the compound of formula 3 is substantially complete, the resulting product is then isolated and purified by conventional procedures. In one embodiment the compound of formula 3 is obtained in solution.

The second step of the process is an oxime-forming step, which involves combining one equivalent of the aldehyde of formula 3 with one or more equivalents of hydroxylamine or a salt thereof to form an oxime of formula 4.

Typically, the compound of formula 3 and the hydroxylamine or a salt thereof are combined in the presence of an excess amount of a suitable base to form a reaction mixture. In one embodiment, from about 1 to about 2 equivalents of the hydroxylamine or a salt thereof are used based on the amount of compound of formula 3; and in another embodiment, about 1.4 to about 1.5 equivalents are used.

An excess amount of base is used, typically from about 3.0 to about 6.0 equivalents based on the amount of compound of formula 3, and in one embodiment, about 3.0 to about 4.0 equivalents. In one embodiment the base is an alkali metal carbonate such as sodium bicarbonate.

Formation of the oxime of formula 4 is typically conducted at a temperature ranging from about 20° C. to about 60° C.; and in one embodiment at a temperature ranging from about 30° C. to about 50° C. for about 20 to about 28 hours, and in one embodiment for about 22 to 26 hours, or until formation of the oxime is substantially complete. When formation of the oxime is substantially complete, the resulting product is then isolated and purified by conventional procedures.

The third step of the process is the reduction of the oxime to a primary amine, and involves reacting the oxime of formula 4 with a reducing agent to form an amine of formula II or a salt thereof.

Exemplary reducing agents are those suited for reducing the oxime to an amine, and include hydrogen/Raney nickel, palladium on carbon (Pd/C), and Zn—HCl. Typically, the oxime of formula 4 and the reducing agent are combined in a polar, protic solvent and an amine base to form a reaction mixture. Formation of the amine is typically conducted at ambient temperature for about 1 to about 5 hours, and in one embodiment for about 2 to 4 hours, or until formation of the amine is substantially complete. In one embodiment, the amine base is ammonium hydroxide and the solvent is ethanol.

When formation of the amine is substantially complete, the resulting product is then isolated and purified by conventional procedures. The amine is optionally crystallized by treatment with heptanes to complete dissolution, cooling to effect crystallization, and isolating the resulting solids to yield the crystalline material. Typically the cooling step is done at a temperature ranging from about 0° C. to about 10° C., and in one embodiment at a temperature ranging from about 2° C. to 6° C., for about 22 to 26 hours, or until formation of crystals. Upon completion of the crystallization step, the crystalline compound of formula II or a salt thereof can be isolated from the reaction mixture by any conventional means.

The process for preparing a compound of formula III or a salt thereof is conducted in five steps. The first, second and third steps are described above with reference to the process of preparing compound of formula II.

The fourth step of the process is a coupling step, which involves reacting one equivalent of the amine of formula II or a salt thereof with one or more equivalents of a carboxylic acid of formula 5 or a salt thereof, in the presence of one or more equivalents of an amine-carboxylic acid coupling reagent to form a compound of formula 6 or a salt thereof.

Carboxylic acids of formula 5 used in the process of the invention are known in the art and are either commercially available or can be prepared by conventional procedures using commercially available starting materials and conventional reagents. For example, see the Preparations described herein as well as U.S. Publication Nos. 2008/0269305 and 2009/0023228, both to Allegretti et al., which describes various methods for preparing such compounds.

Typically, the amine or a salt thereof and the carboxylic acid or a salt thereof are combined in an inert diluent in the presence of a coupling reagent to form a reaction mixture. In one embodiment, from about 1 to about 2 equivalents of the carboxylic acid are used based on the amount of amine; and in another embodiment, about 1.1 to about 1.3 equivalents are used. In one embodiment, from about 1 to about 2 equivalents of the coupling reagent are used based on the amount of amine; and in another embodiment, about 1.1 to about 1.3 equivalents are used. Exemplary inert diluents include dichloromethane and isopropyl acetate.

Suitable amine-carboxylic acid coupling reagents include (2-(6-chloro-1H-benzotriazole-1-yl)-1,1,3,3-tetramethylaminium hexafluorophosphate) (HCTU), benzotriazol-1-yloxytris(dimethylamino)phosphonium hexafluorophosphate (BOP), benzotriazol-1-yloxytripyrrolidinophosphonium hexafluorophosphate (PyBOP), O-(7-azabenzotriazol-1-yl-N,N,N',N'-tetramethyluronium hexafluorophosphate (HATU), dicyclohexylcarbodiimide (DCC), N-(3-dimethylaminopropyl)-N'-ethylcarbodiimide (EDC), carbonyldiimidazole (CDI), and the like; and in one particular embodiment, the coupling reagent is HCTU.

The coupling reaction is typically conducted at a temperature ranging from about −5° C. to about 5° C.; and in one embodiment at a temperature ranging from about −1° C. to about 3° C. for about 5 to about 15 hours, or until formation of the compound of formula 6 is substantially complete. The pH of the reaction mixture is adjusted to about 5 to about 5 by addition of a suitable acid, such as 1N hydrochloric acid. When formation of the compound of formula 6 is substantially complete, the resulting product is then isolated and purified by conventional procedures.

The fifth step of the process is a deprotection step, which involves removing the carboxylic acid protecting group, P, from the compound of formula 6 or a salt thereof, to form a compound of formula III or a salt thereof.

Standard deprotection techniques and reagents are used to remove the P group, and may vary depending upon which group is used. For example, NaOH is commonly used when P is methyl, an acid such as TFA or HCl is commonly used when P is t-butyl, and catalytic hydrogenation condition such as $H_2$ (1 atm) and 10% Pd/C in alcoholic solvent ("$H_2$/Pd/C") may be used when P is benzyl. In one particular embodiment, TFA is used.

Typically, the compound of formula 6 or a salt thereof and the deprotecting reagent are combined in an inert diluent. An excess amount of reagent is used; in one embodiment from about 10 to about 30 equivalents of the reagent are used based on the amount of the compound of formula 6. In one embodiment, the inert diluent is anhydrous, such as tetrahydrofuran, dichloromethane, N,N-dimethylformamide, and 1,4-dioxane.

This deprotection step is typically conducted at a temperature ranging from about 10° C. to about 30° C.; and in one embodiment at a temperature ranging from about 15° C. to about 25° C. for about 12 to about 20 hours, and in one embodiment for about 14 to 18 hours, or the reaction is substantially complete. The pH of the reaction mixture is then adjusted to about 6 to about 7 by addition of a suitable base, such as aqueous potassium carbonate.

When formation of the compound of formula III is substantially complete, the resulting product is then isolated and purified by conventional procedures. The compound of formula III is optionally crystallized by treatment with isopropyl acetate to complete dissolution, cooling to effect crystallization, and isolating the resulting solids to yield the crystalline material. Typically the cooling step is done at a temperature ranging from about 0° C. to about 10° C., and in one embodiment at a temperature ranging from about 2° C. to 6° C., for about 14 to 18 hours, or until formation of crystals. Upon completion of the crystallization step, the crystalline compound of formula III can be isolated from the reaction mixture by any conventional means.

The compound of formula III can then be used to prepare compound of formula IV, by converting the thioester group, —SC(O)—$R^4$ to a thiol, —SH. This can be done by conventional methods such as by treatment with bases such as sodium hydroxide, sodium methoxide, primary alkylamines, and hydrazine.

Crystalline Properties

One exemplary compound of formula I is 4'-(4-bromo-2-ethoxy-5-formylimidazol-1-ylmethyl)-3'-fluorobiphenyl-2-carboxylic acid tert-butyl ester, which is represented by formula Ia:

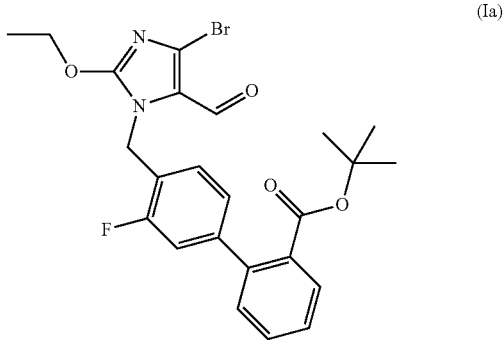

(Ia)

In one embodiment, the compound of formula Ia is in a crystalline form.

One exemplary compound of formula II is 4'-(5-aminomethyl-2-ethoxy-4-ethylimidazol-1-ylmethyl)-3'-fluorobiphenyl-2-carboxylic acid t-butyl ester, which is represented by formula IIa:

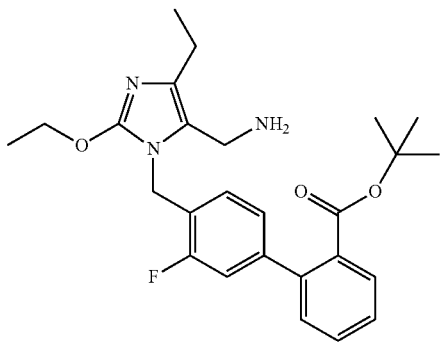

(IIa)

In one embodiment, the compound of formula IIa is in a crystalline form. In another embodiment, the crystalline form is not associated with any counterions and is referred to as a freebase crystalline form.

One exemplary compound of formula III is 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid, which is represented by formula IIIa:

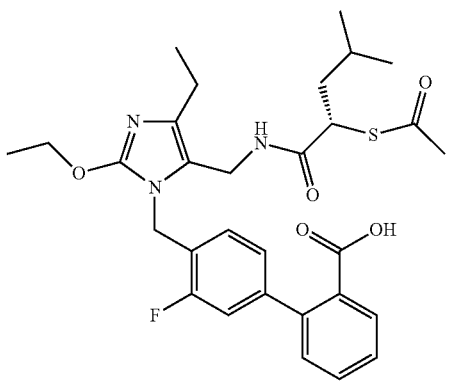

(IIIa)

In one embodiment, the compound of formula IIIa is in a crystalline form. In another embodiment, the crystalline form is a zwitterion.

As is well known in the field of powder x-ray diffraction, relative peak heights of PXRD spectra are dependent on a number of factors relating to sample preparation and instrument geometry, while peak positions are relatively insensitive to experimental details. A PXRD pattern was obtained as set forth in Example 4. Thus, in one embodiment, the crystalline compounds of the invention are characterized by a PXRD pattern having certain peak positions.

The crystalline form of 4'-(5-aminomethyl-2-ethoxy-4-ethylimidazol-1-ylmethyl)-3'-fluorobiphenyl-2-carboxylic acid t-butyl ester (formula IIa) is characterized by a PXRD pattern in which the peak positions are substantially in accordance with those shown in FIG. 1. Those peaks are listed below, in order of descending relative intensity.

| I % | 2-Theta |
|---|---|
| 100 | 31.91 |
| 87 | 20.63 |
| 72 | 10.43 |

-continued

| I % | 2-Theta |
|---|---|
| 57 | 15.65 |
| 53 | 23.96 |
| 32 | 18.20 |
| 25 | 24.86 |
| 24 | 12.74 |
| 24 | 23.03 |
| 18 | 5.24 |
| 16 | 14.90 |
| 14 | 21.71 |

Thus, in one embodiment, the crystalline form of formula IIa is characterized by a powder x-ray diffraction (PXRD) pattern comprising diffraction peaks at 2θ values of 5.24±0.2, 10.43±0.2, 15.65±0.2, 20.63±0.2, and 31.91±0.2; and further characterized by comprising one or more additional diffraction peaks at 2θ values selected from 12.74±0.2, 14.90±0.2, 18.20±0.2, 21.71±0.2, 23.03±0.2, 23.96±0.2, and 24.86±0.2.

Figure 3:
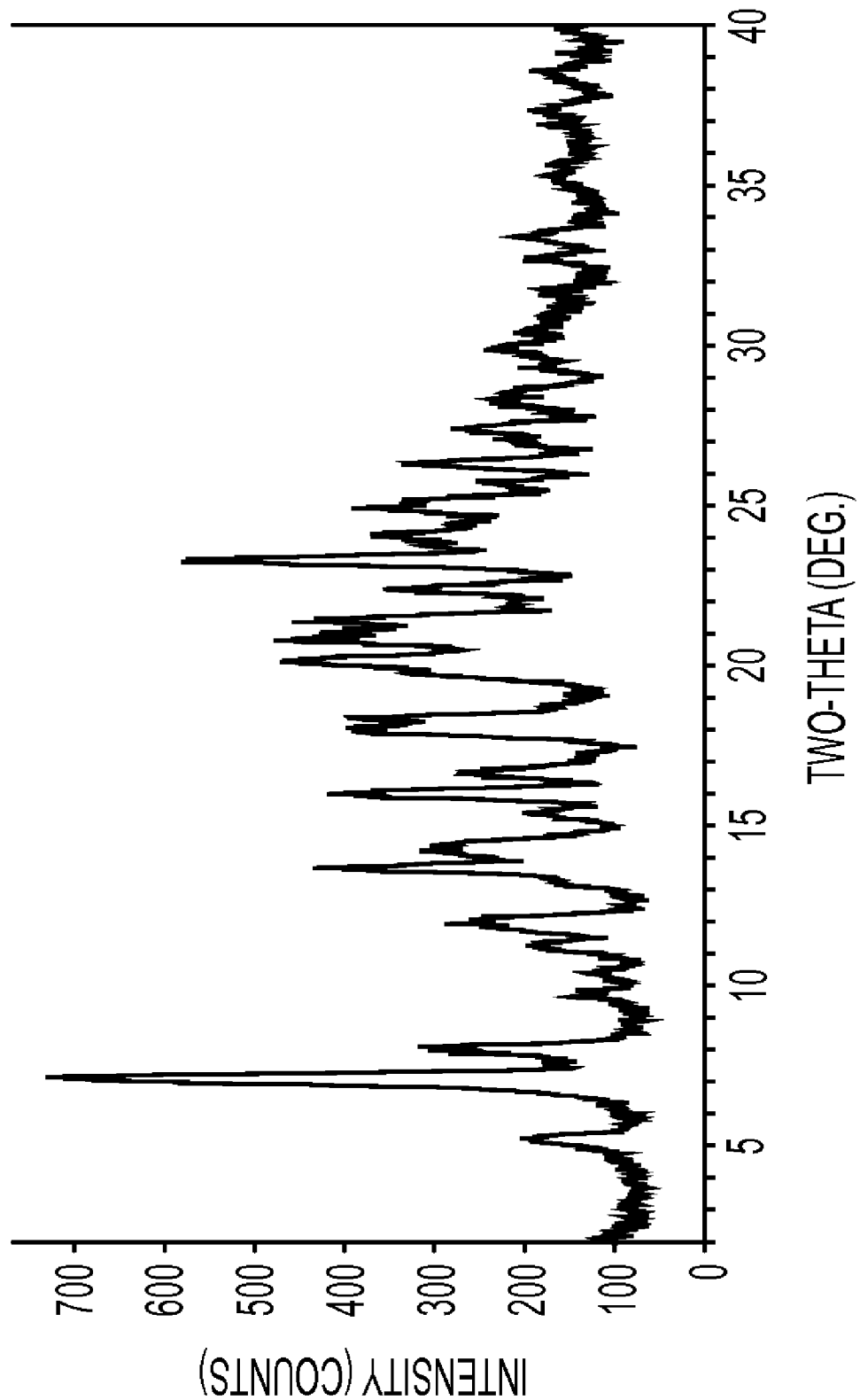
FIG. 3 shows a powder x-ray diffraction (PXRD) pattern of the crystalline form of 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid (formula IIIa).

The crystalline form of 4'-{5-[((S)-2-acetylsulfanyl-4-methylpentanoylamino)-methyl]-2-ethoxy-4-ethylimidazol-1-ylmethyl}-3'-fluorobiphenyl-2-carboxylic acid (formula IIIa) is characterized by a PXRD pattern in which the peak positions are substantially in accordance with those shown in FIG. 3. Those peaks are listed below, in order of descending relative intensity.

| I % | 2-Theta |
|---|---|
| 100 | 7.16 |
| 61 | 23.24 |
| 57 | 20.12 |
| 53 | 13.68 |
| 48 | 15.98 |
| 41 | 8.10 |
| 36 | 20.78 |
| 30 | 26.28 |
| 26 | 12.06 |
| 24 | 16.62 |
| 21 | 5.24 |
| 13 | 11.26 |

Thus, in one embodiment, the crystalline form of formula IIIa is characterized by a powder x-ray diffraction (PXRD) pattern comprising diffraction peaks at 2θ values of 5.24±0.2, 7.16±0.2, 13.68±0.2, and 15.98±0.2; and further characterized by comprising one or more additional diffraction peaks at 2θ values selected from 8.10±0.2, 11.26±0.2, 12.06±0.2, 16.62±0.2, 20.12±0.2, 20.78±0.2, 23.24±0.2, and 26.28±0.2.

Figure 2:
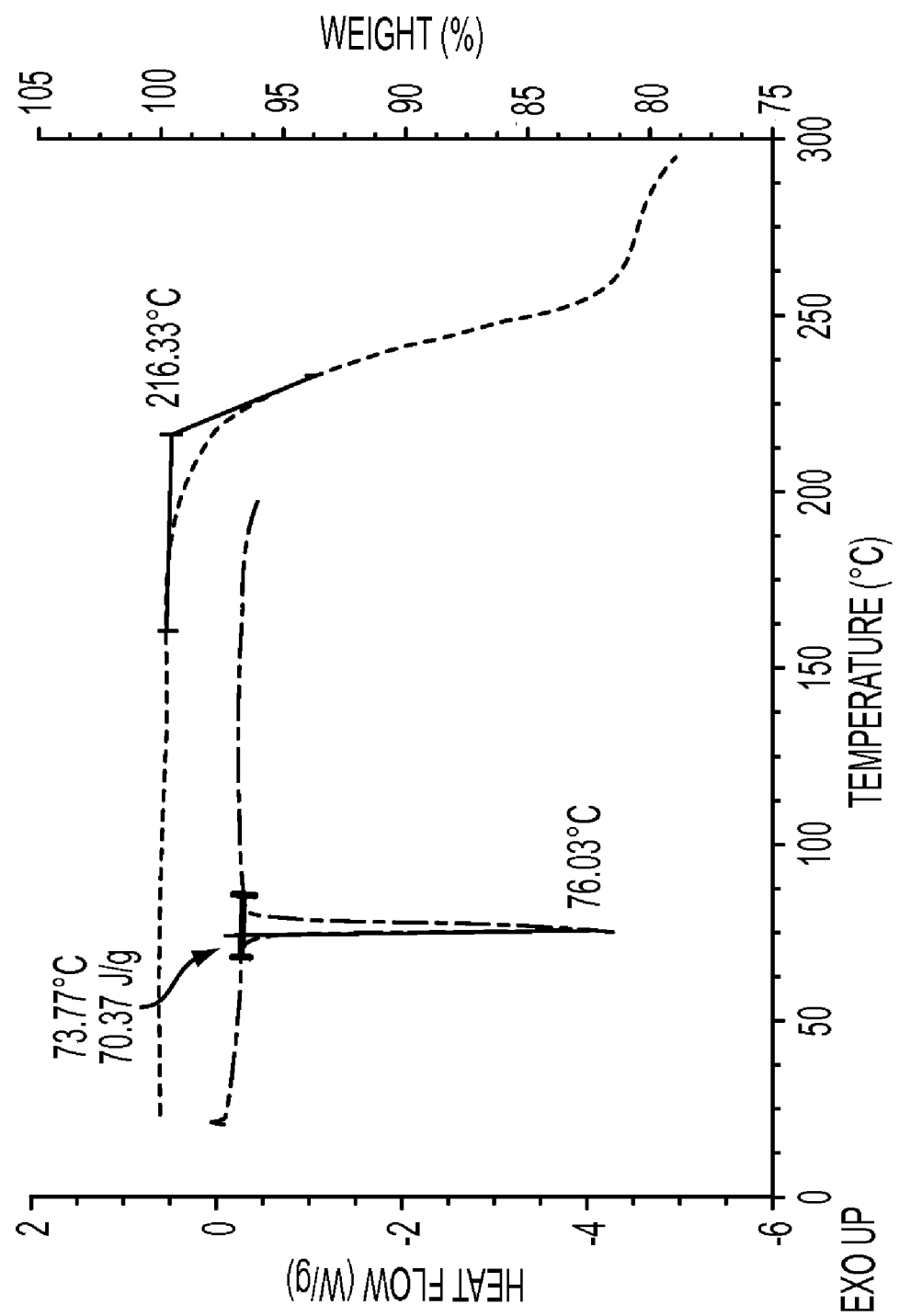
FIG. 2 shows a differential scanning calorimetry (DSC) thermograph and a thermal gravimetric analysis (TGA) for this crystalline compound.
Figure 4:
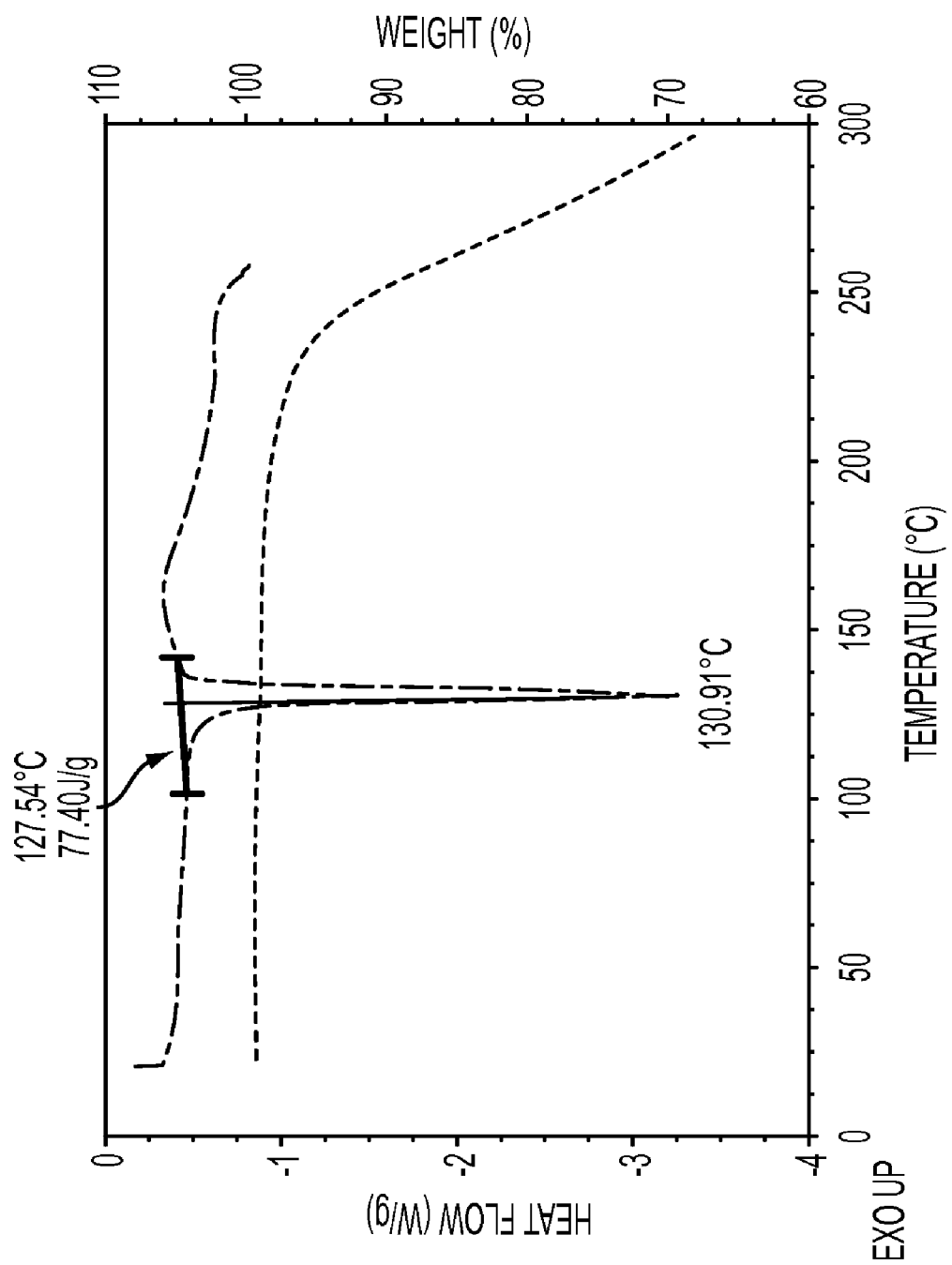
FIG. 4 shows a DSC thermograph and a TGA for this crystalline compound.

Differential scanning calorimetry (DSC) traces were obtained as set forth in Example 5. Thus, in one embodiment, the crystalline compounds of the invention are characterized by their DSC thermographs. In one embodiment, the crystalline form of formula IIa is characterized by a DSC thermograph which shows a melting point of about 76.0° C., with no significant thermal decomposition below about 150.0° C., as seen in FIG. 2. In one embodiment, the crystalline form of formula IIIa is characterized by a DSC thermograph which shows a melting point of about 130.9° C., with no significant thermal decomposition below about 150.0° C., as seen in FIG. 4.

Thermogravimetric analysis (TGA) was performed on the crystalline compounds of the invention as described in Example 5. Thus, in one embodiment, the crystalline compounds of the invention are characterized by their TGA trace. In one embodiment, the crystalline form of formula IIa is characterized by a TGA trace which shows a loss of solvents and/or water (<0.5%) at temperatures below about 150° C. (which is significantly higher than the melting point), as seen in FIG. 2. In one embodiment, the crystalline form of formula Ma is characterized by a TGA trace which shows a loss of solvents and/or water (<0.5%) at temperatures below about 150° C. (which is significantly higher than the melting point), as seen in FIG. 4.

These properties of the crystalline compounds of the invention are further illustrated in the Examples below.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard generally accepted meaning:

| | |
|---|---|
| AcOH | acetic acid |
| Bu₄NBr | tetrabutylammonium bromide |
| DCC | 1,3-dicyclohexylcarbodiimide |
| DCM | dichloromethane or methylene chloride |
| DIPEA | N,N-diisopropylethylamine |
| DMAP | 4-dimethylaminopyridine |
| DMF | N,N-dimethylformamide |
| DMSO | dimethyl sulfoxide |
| DTT | 1,4-dithiothreitol |
| EtOAc | ethyl acetate |
| EtOH | ethanol |
| HCTU | (2-(6-chloro-1H-benzotriazole-1-yl)-1,1,3,3-tetramethylaminium hexafluorophosphate) |
| IPAc | isopropyl acetate |
| MeCN | acetonitrile |
| MeOH | methanol |
| MTBE | methyl t-butyl ether |
| NaOMe | sodium methoxide |
| NBS | N-bromosuccinimide |
| TFA | trifluoroacetic acid |
| THF | tetrahydrofuran |

Unless noted otherwise, all materials, such as reagents, starting materials and solvents, were purchased from commercial suppliers (such as Sigma-Aldrich, Fluka Riedel-de Haën, Strem Chemicals, Inc., and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% water/2% MeCN/1.0 mL/L TFA; solvent B was 90% MeCN/10% water/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

5-Bromo-2-ethoxy-3H-imidazole-4-carbaldehyde

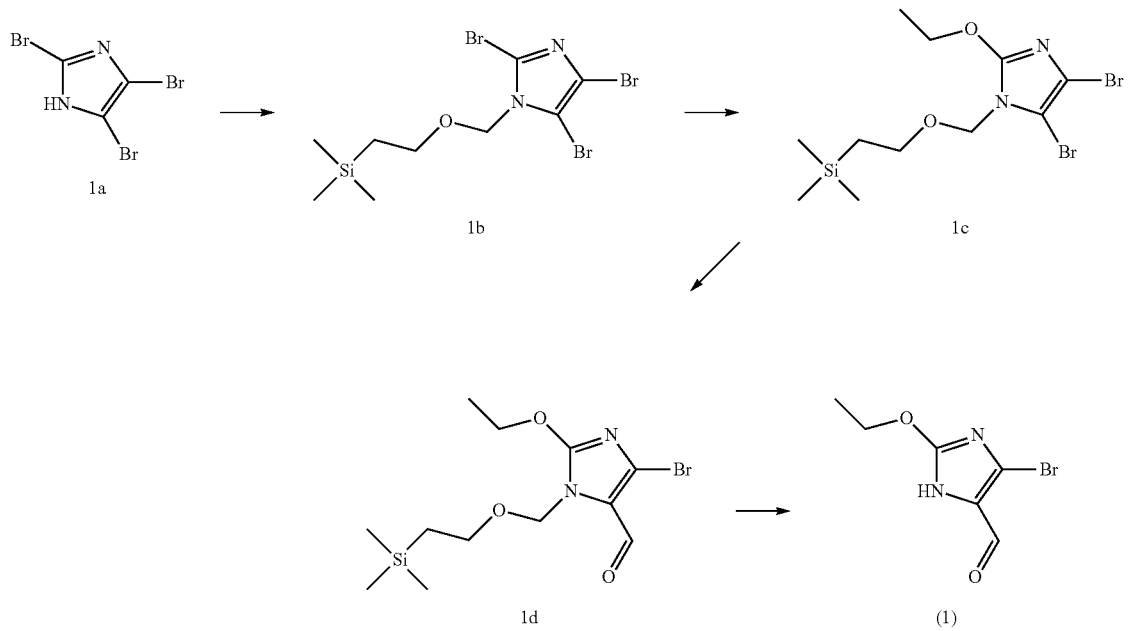

2,4,5-Tribromo-1H-imidazole (1a) (98.7 g, 324 mmol, 1.0 eq) was dissolved into 1.20 L of DCM and cooled to 0° C. To this was added DIPEA (62 mL, 360 mmol, 1.1 eq) followed by the slow addition of [β-(trimethylsilyl)ethoxy]methyl chloride (60.2 mL, 340 mmol, 1.05 eq). The solution was slowly warmed to room temperature. After 2 hours the mixture was washed with 1M $H_3PO_4$/saturated aqueous NaCl (1:10; 2×600 mL). The organic layer was dried over $MgSO_4$, and evaporated to dryness, yielding intermediate (1b) as faint yellow liquid that solidified on standing (137 g).

Intermediate (1b) (130 g, 290 mmol, 1.0 eq) was dissolved into anhydrous EtOH (650 mL). To this was slowly added potassium t-butoxide (98.6 g, 879 mmol, 3.0 eq) and the mixture was heated to reflux for 16 hours. The mixture was then cooled to room temperature, filtered and concentrated. The resulting oil was dissolved in EtOAc (800 mL) and washed with saturated $NaHCO_3$ (400 mL). The layers were separated and the organic was washed with saturated aqueous NaCl, dried over $MgSO_4$, filtered and concentrated, yielding intermediate (1c) as a brown oil (115.3 g). MS m/z: [M+H$^+$] calcd for $C_{11}H_{20}Br_2N_2O_2Si$, 401.9 found 401.2.

Intermediate (1c) (69.5 g, 174 mmol, 1.0 eq) was dissolved in anhydrous THF (600 mL) and cooled to −78° C. under nitrogen. A 2.5M solution of n-butyllithium in hexanes (72.9 mL, 180 mmol, 1.05 eq) was added dropwise and the mixture was stirred at −78° C. for 10 minutes. DMF (40 mL, 520 mmol, 3.0 eq) was then added and the mixture was stirred at −78° C. for 15 minutes and was then warmed to room temperature. The reaction was quenched with water (10 mL), diluted with EtOAc (600 mL) and was washed with water (100 mL), saturated aqueous NaCl, dried over $MgSO_4$ and concentrated under reduced pressure. The recovered material was purified by silica gel chromatography (15-30% EtOAc: hexanes) to produce intermediate (1d) as a pale yellow oil (45 g).

Intermediate (1d) (105.8 g, 303 mmol, 1.0 eq) was cooled at 0° C. in ice. TFA (300 mL) was added and the mixture was stirred at 0° C. for 15 minutes, then warmed to room temperature. After 90 minutes the mixture was concentrated under reduced pressure and redissolved in EtOAc (700 mL). The organic was washed with saturated bicarbonate (2×600 mL), saturated aqueous NaCl, dried over $MgSO_4$, and concentrated under reduced pressure to produce a yellow solid. The material was suspended in hexanes (300 mL) and stirred at 0° C. for 30 minutes. The material was filtered and the solid was washed with cold hexanes (150 mL) to yield the title compound (1) as a pale white solid (61.2 g). $^1$H-NMR (CDCl$_3$) δ (ppm): 1.4 (m, 3H), 4.5 (m, 2H), 5.2 (s, 1H), 9.2 (d, 1H).

Preparation 2

4'-Bromomethyl-3'-fluorobiphenyl-2-carboxylic Acid t-Butyl Ester

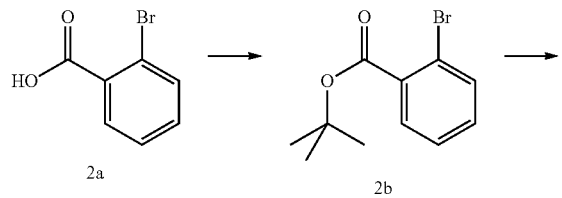

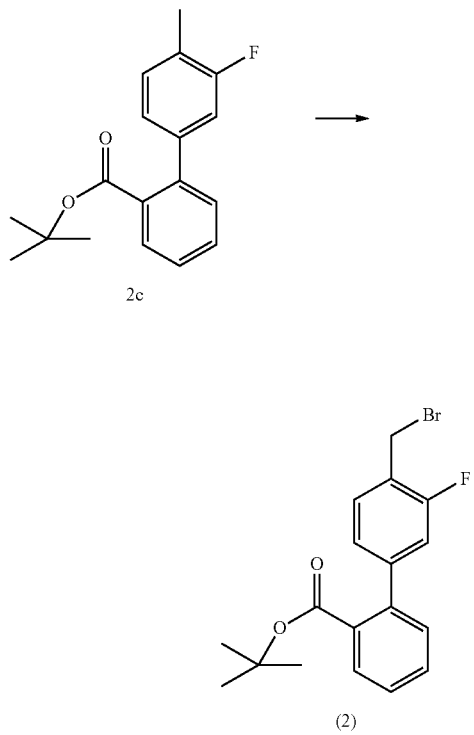

To a solution of 1.0M DCC in DCM (800 mL, 800 mol) cooled at 0° C. was added 2-bromobenzoic acid (2a) (161 g, 800 mmol) followed by DMAP (9.0 g, 740 mmol) and t-butyl alcohol (82.4 mL, 880 mmol). The mixture was stirred at room temperature for 10 minutes, then warmed to room temperature and stirred. After 16 hours, the mixture was then filtered. The organic was washed with saturated $NaHCO_3$ (400 mL), saturated aqueous NaCl, dried over $MgSO_4$, filtered and concentrated under reduced pressure to produce the crude intermediate (2b) as an oil (228.8 g).

The crude intermediate (2b) (109.6 g, 426 mmol) and 3-fluoro-4-methylphenyl-boronicacid (72.2 g, 449 mmol) were suspended in isopropyl alcohol (360 mL, 4.7 mmol). A 2.0M solution of sodium carbonate in water (360 mL, 720 mmol) was added and the mixture was degassed under nitrogen. Tetrakis(triphenylphosphine)palladium(0) (4.9 g, 4.3 mmol) was then added and the mixture was stirred at 90° C. for 46 hours. The mixture was cooled to room temperature, diluted with EtOAc (800 mL), and the layers were separated. The organic was washed with saturated aqueous NaCl and concentrated under reduced pressure. The recovered oil was purified by silica gel chromatography (3×4-6% EtOAc:hexanes) to yield intermediate (2c) as a clear oil (93.3 g).

Intermediate (2c) (89.8 g, 314 mmol, 1.0 eq) was dissolved in $CCl_4$ (620 mL, 6.4 mol) and was degassed under nitrogen. NBS (55.8 g, 314 mmol) was added, followed by benzoyl peroxide (1.5 g, 6.3 mmol) and the mixture was heated at 90° C. under nitrogen for 7 hours. The reaction was cooled in an ice bath, filtered, and concentrated under reduced pressure. The recovered oil was triturated with 150 mL of 3% EtOAc: hexanes. The solution was chilled at −20° C. for 2 hours, then filtered and washed with cold 3% EtOAc:hexanes solution (200 mL) to yield the title compound (2) as an off white solid (88.9 g). $^1$H-NMR (CDCl$_3$) δ (ppm): 1.3 (m, 9H), 4.6 (s, 2H), 7.0-7.1 (m, 2H), 7.3 (dd, 1H), 7.4 (m, 1H), 7.5 (m, 1H), 7.8 (dd, 1H).

Example 1

Crystalline 4'-(5-Aminomethyl-2-ethoxy-4-ethylimidazol-1-ylmethyl)-3'-fluorobiphenyl-2-carboxylic Acid t-Butyl Ester

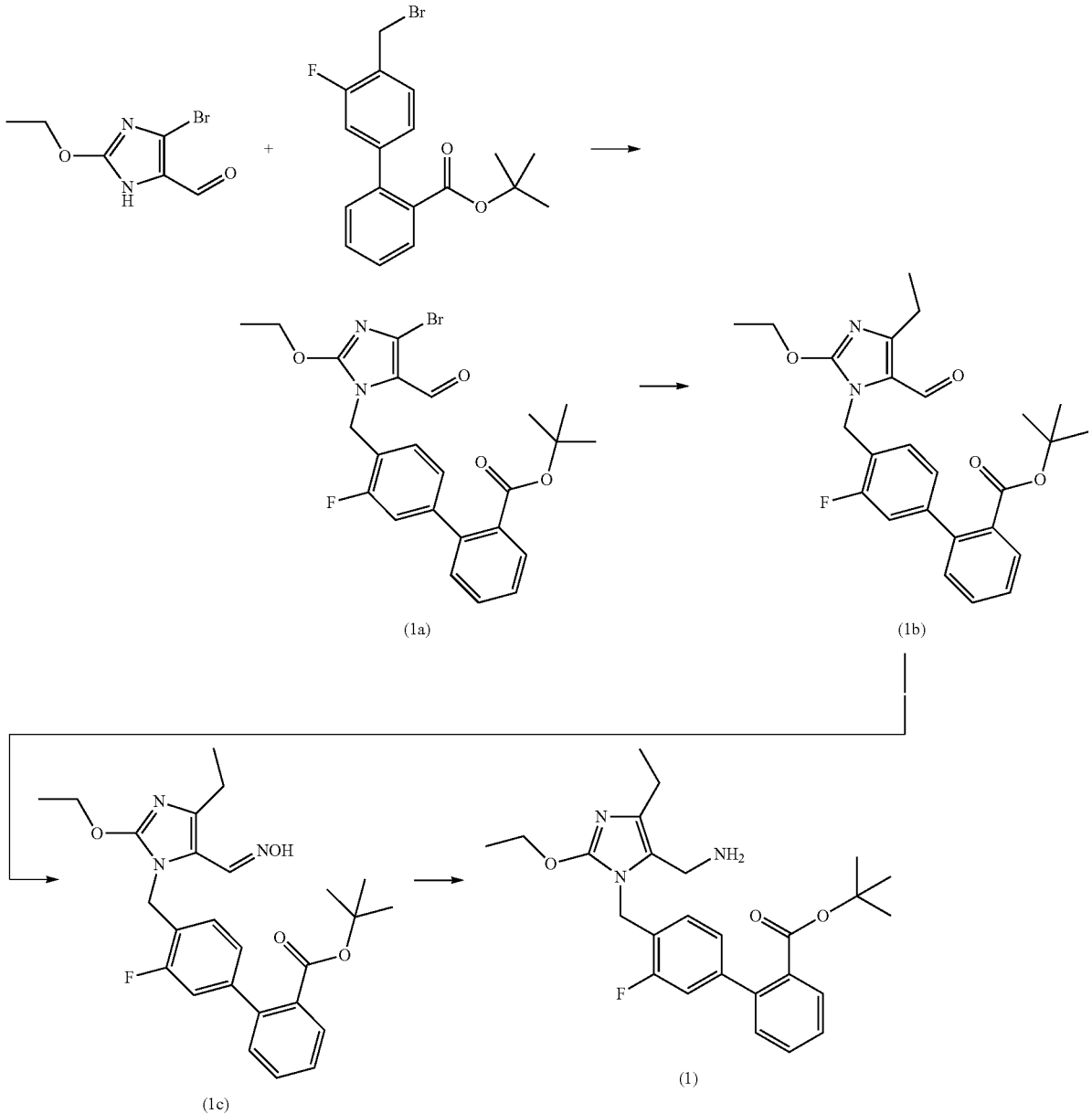

5-Bromo-2-ethoxy-3H-imidazole-4-carbaldehyde (22.0 g, 100 mmol, 1.1 eq.), 4'-bromomethyl-3'-fluorobiphenyl-2-carboxylic acid t-butyl ester (33.0 g, 90 mmol, 1 eq.), and Bu$_4$NBr (1.6 g, 5 mmol, 0.05 eq.) were dissolved in toluene (400 mL) and 1N NaOH (120 mL, 120 mmol, 1.2 eq.). The resulting mixture was stirred at 27° C. for 48-60 hours. The toluene layer was separated, washed with water (2×200 mL), then removed by distillation. EtOH (350 mL) was added to the residue and the mixture was heated to 50-60° C. until the solids dissolved. The mixture was cooled to room temperature over 4 hours, then cooled to 4° C. and stirred at 4° C. for 4 hours. The solids were filtered off, washed with cold EtOH (60 mL) and dried at room temperature under vacuum for 24 hours to yield intermediate (1a) (~39 g).

Intermediate (1a) (20.0 g, 40 mmol, 1 eq.), potassium ethyl trifluoroborate (7.1 g, 52 mmol, 1.3 eq.), palladium(II) acetate (224 mg, 1 mmol, 0.025 eq.), cataCXium® A (butyldi-1-adamantylphosphine; CAS# 321921-71-5; 538 mg, 1.45 mmol, 0.04 eq.), and Cs$_2$CO$_3$ (45 g, 138 mmol, 3.45 eq.) were dissolved in toluene (240 mL) and water (80 mL). The mixture was flushed with nitrogen (3×) under vacuum, then heated to 90° C. for 16 hours. The mixture was then cooled to room temperature and the layers were separated. The organic layer was washed with water (2×200 mL) then distilled under reduced pressure to yield an oil. The oil was dissolved in EtOH (240 mL). Water (80 mL) was added and the mixture was stirred for 30 minutes. The mixture was filtered to remove solids, the solids were washed with 75% EtOH (130 mL), and the filtrate collected to yield intermediate (1b) in an EtOH solution, which was used directly in the next step.

The EtOH solution of intermediate (1b) (10 mmol, 1 eq.) was combined with hydroxylamine hydrochloride (27.2 g, 52 mmol, 1.3 eq.) and NaHCO₃ (35.2 g, 3.45 eq.). The mixture was stirred at 40° C. for 24 hours, then cooled to room temperature. The precipitant was filtered off, washed with 75% EtOH (100 mL) and 50% EtOH (200 mL), then dried under reduced pressure at 30° C. for 24 hours to yield intermediate (1c) (15 g).

Intermediate (1c) (5 g) was combined with EtOH (100 mL), NH₄OH (28%, 6 mL), and Raney nickel (wet 10 g) to form a slurry. The mixture was degassed under nitrogen (3×), degassed under hydrogen (3×), then stirred under hydrogen (1 atm) for 3 hours. The mixture was filtered to remove the catalyst and the solids were washed with EtOH (20 mL). The filtrate was then treated with charcoal (0.5 g) and filtered again. The filtrate was then distilled under vacuum to yield an oil. Heptanes were added (50 mL) and the mixture distilled to an oil (2×). The remaining oil was dissolved in heptanes (60 mL) by heating the mixture and stirring at 4° C. for 24 hours. The solids were then filtered, washed with cold heptanes (10 mL), and dried at room temperature for 24 hours to yield the title compound as a crystalline material (3.8 g).

Preparation 3

(S)-2-Acetylsulfanyl-4-methylpentanoic Acid

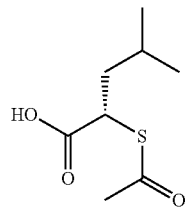

D-Leucine (8.2 g, 62.7 mmol) was dissolved in 3.0M HBr in water (99 mL, 0.3 mol) and cooled to 0° C. A solution of NaNO₂ (6.9 g, 100 mmol) in water (11.3 mL, 627 mmol) was slowly added over 20 minutes. The mixture was stirred at 0° C. for 3 hours and then extracted twice with ethyl ether, washed with water then saturated aqueous NaCl, dried over MgSO₄, filtered, and concentrated to afford (R)-2-bromo-4-methylpentanoic acid (11.5 g) as an off-yellow oil. This was taken on to the next step without further purification.

Thioacetic acid (4.2 g, 54.4 mmol) and DMF (100 mL, 1.0 mol) were combined, and the mixture cooled in an ice bath. Sodium carbonate (5.8 g, 54.4 mmol) was added. After 30 minutes, (R)-2-bromo-4-methylpentanoic acid (10.1 g, 51.8 mmol) in DMF (20 mL) was added dropwise and the mixture was stirred at 0° C. to room temperature over 6 hours. The mixture was diluted with 100 mL EtOAc and extracted with 100 mL of a 1:1 1N HCl: saturated aqueous NaCl solution. The layers were separated and the aqueous phase was extracted with additional EtOAc (100 mL). The organics were combined, washed with saturated aqueous NaCl, dried over MgSO₄, filtered, and concentrated under reduced pressure. The recovered oil was dissolved into diisopropyl ether (45 mL, 320 mmol) and chilled at 0° C. Dicyclohexylamine (10.1 mL, 50.7 mmol) was added dropwise and the solid was allowed to crash out of solution. After stirring for an additional 30 minutes the material was filtered and washed with 75 mL cold diisopropyl ether. The recovered solid (14 g) was suspended in 100 mL EtOAc. 150 mL of 5% KHSO₄ was added and the layers were separated. The organic was washed with saturated aqueous NaCl, dried over MgSO₄, filtered, and concentrated under reduced pressure. The recovered oil was then azeotroped (3×25 mL toluene) to yield the title compound (6.1 g) as a dicyclohexylamine salt.

Example 2

Crystalline 4'-{5-[((S)-2-Acetylsulfanyl-4-methyl-pentanoylamino)methyl]-2-ethoxy-4-ethylimidazol-1-ylmethyl}-3'-fluorobiphenyl-2-carboxylic Acid

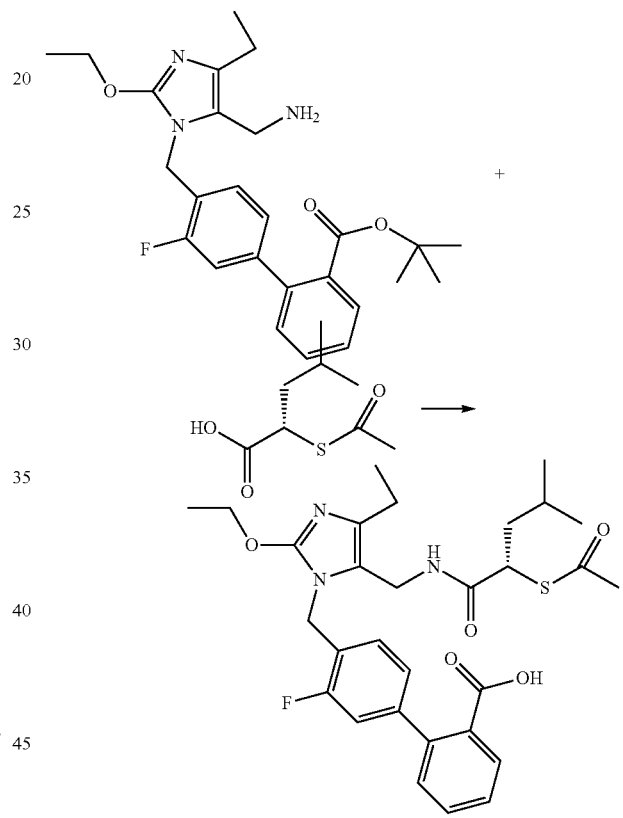

Crystalline 4'-(5-aminomethyl-2-ethoxy-4-ethylimidazol-1-ylmethyl)-3'-fluorobiphenyl-2-carboxylic acid t-butyl ester (dicyclohexylamine salt; 18 g, 40 mmol, 1 eq.), (S)-2-acetylsulfanyl-4-methylpentanoic acid (18 g, 48 mmol, 1.2 eq.), and HCTU (19 g, 48 mmol, 1.2 eq.) were combined in a pre-chilled vessel (0° C. for 10 minutes) and cold DCM (240 mL) was added. The mixture was stirred at 1±2° C. for 5-15 hours. 4% NaHCO₃ (200 mL) was added and the mixture was stirred for 15 minutes. The DCM layer was separated and distilled to ~100 mL. IPAc (150 mL) was added and distill to 150 mL. Additional IPAc (200 mL) was added and the mixture was washed with 4% NaHCO₃ (2×200 mL) and water (200 mL). The solution was stirred with 15% NH₄Cl (300 mL) for 15 minutes, the pH was adjusted to 5.5 with 1N HCl, and then stirred for 1 hour. The solids were filtered off. The filtrate was washed with IPAc (50 mL), and the IPAc layer separated. The IPAc layer was stirred with 15% NH₄Cl (200 mL) for 3 hours and any solids filtered off. The filtrate was washed with saturated aqueous NaCl (150 mL) and distilled under vacuum to ~60 mL. DCM (50 mL) was added and distilled off. DCM (200 mL) was added and the mixture was cooled 0-5° C. TFA (70 mL) was added slowly (slightly exothermic) at below 15° C., and the mixture was stirred at 20° C. for 16 hours. The mixture was concentrated to ~150 ml, and IPAc (150 mL) was added. The mixture was distilled to ~150 mL. Additional IPAc (150 mL) was added, and again distilled to ~150 mL. IPAc (200 mL) was added and the resulting solution was slowly added to pre-cooled $K_2CO_3$ (52 g) in water (250 mL) at below 10° C. (mildly exothermic, pH>7 must >6 during quench) over 15 minutes. The pH was monitored during the transfer, and additional base (8 g) was added when the pH dropped below 6. The IPAc layer was separated and washed with saturated aqueous NaCl (150 mL). The IPAc solution was distilled to ~50 mL. MTBE (100 mL) was added and the mixture distilled to ~50 mL. Additional MTBE (100 mL) was added and the mixture was stirred at room temperature for 3 hours, forming a slurry, which was then stirred at 4° C. for 16 hours. The solids were filtered off and washed with MTBE/diisopropyl ether (1:1; 100 mL). The solids were then dried at room temperature for 60 hours under nitrogen to yield the title compound as a crystalline material (18.2 g).

Example 3

Crystalline 4'-{2-Ethoxy-4-ethyl-5-[((S)-2-mercapto-4-methylpentanoylamino)methyl]imidazol-1-ylmethyl}-3'-fluorobiphenyl-2-carboxylic Acid

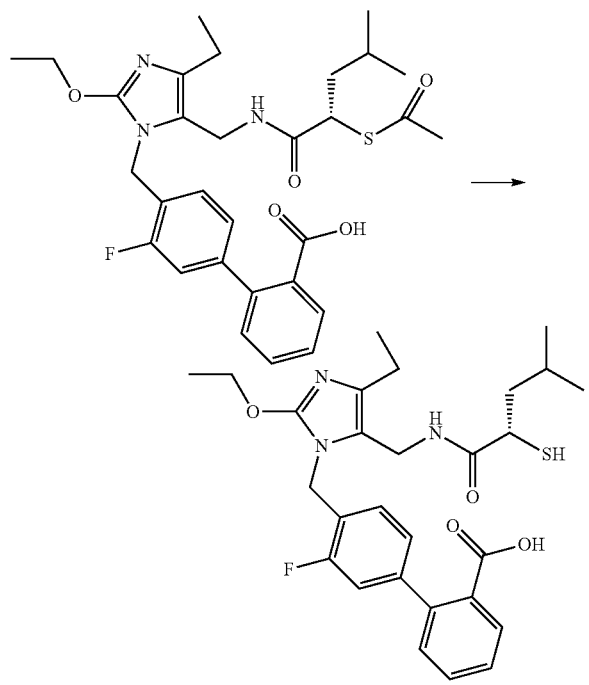

Crystalline 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid (2.3 g, 4 mmol, 1 eq.) and DTT (62 mg, 0.4 mmol, 0.1 eq.) was dissolved in MeOH (30 mL). The resulting solution was degassed with nitrogen (3 times) and cooled at 0° C. NaOMe (25% in MeOH, 1.7 mL) was added and the mixture was stirred at 0° C. for 30 minutes. AcOH (3 g, 50 mmol, 4 eq.) was added to quench the reaction at 0° C. The mixture was warmed to 20° C. Deionized water (10 mL) was added slowly. The mixture was stirred at 20° C. for 3 hours and then stirred at 4° C. for 1 hour until precipitates were formed. The solids were filtered and washed with MeOH/$H_2O$ (2:1; 30 mL), then dried under nitrogen at 20° C. for 48 hours to yield the title crystalline compound (1.2 g).

Example 4

Powder X-Ray Diffraction

Powder X-ray diffraction patterns were obtained with a Rigaku Miniflex PXRD diffractometer using Cu Kα (30.0 kV, 15.0 mA) radiation. The analysis was performed with the goniometer running in continuous-scan mode of 2° (2θ) per min with a step size of 0.03° over a range of 2 to 40° in two-theta angle. Samples were prepared on quartz specimen holders as a thin layer of powdered material. The instrument was calibrated with a silicon metal standard, within ±0.02° two-theta angle.

A representative PXRD pattern for a sample of the crystalline compound of Example 1 is shown in FIG. 1. A representative PXRD pattern for a sample of the crystalline compound of Example 2 is shown in FIG. 3. The numerous intense powder diffraction peaks and relatively flat baseline depicted in FIGS. 1 and 3 strongly indicated that the crystalline compounds of formula IIa and IIIa possessed good crystallinity.

Example 5

Thermal Analysis

Differential scanning calorimetry (DSC) was performed using a TA Instruments Model Q-100 module with a Thermal Analyst controller. Data were collected and analyzed using TA Instruments Thermal Solutions software. A 2.05 mg sample of the crystalline compound of Example 1 was accurately weighed into a covered aluminum pan. After a 5 minute isothermal equilibration period at 22° C., the sample was heated using a linear heating ramp of 10° C./min from 22° C. to 250° C. A representative DSC thermograph is shown in FIG. 2.

The DSC thermograph demonstrates that this crystalline compound has excellent thermal stability with a melting point at about 76.0° C. and no thermal decomposition below 150.0° C. The non-complex thermal profile does not show any undesired endothermic or exothermic peak prior to the melting endotherm at 76.0° C., which suggests that this crystalline solid is most likely an anhydrous crystalline form.

A representative TGA trace is shown in FIG. 2, and indicates that a sample of the crystalline compound of Example 1 lost a small amount (<0.5%) of weight from room temperature to 150.0° C., which is consistent with the loss of residual moisture or solvent.

A 1.12 mg sample of the crystalline compound of Example 2 was similarly evaluated. A representative DSC thermograph is shown in FIG. 4. The DSC thermograph demonstrates that this crystalline compound has excellent thermal stability with a melting point at about 130.9° C. and no thermal decomposition below 150.0° C. The non-complex thermal profile does not show any undesired endothermic or exothermic peak prior to the melting endotherm at 130.9° C., which suggests that this crystalline solid is most likely an anhydrous crystalline form.

A representative TGA trace is shown in FIG. 4, and indicates that a sample of the crystalline compound of Example 1 lost a small amount (<0.5%) of weight from room temperature to 150.0° C., which is consistent with the loss of residual moisture or solvent.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A process for preparing a compound of formula I:

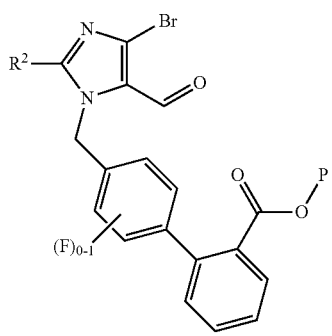

(I)

where $R^2$ is —O—$C_{1-5}$alkyl and P is a carboxylic acid protecting group; the process comprising the step of reacting a compound of formula 1:

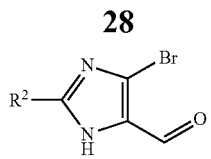

(1)

with a compound of formula 2:

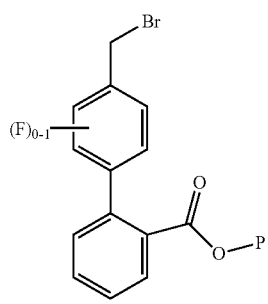

(2)

in an organic diluent and a basic aqueous diluent in the presence of a phase transfer catalyst, where the diluents are substantially immiscible, to form a compound of formula I.

2. The process of claim 1, where the organic diluent is toluene.

3. The process of claim 1, where the basic aqueous diluent is NaOH.

4. The process of claim 1, where the phase transfer catalyst is tetrabutylammonium bromide.

5. The process of claim 1, further comprising the step of preparing a crystalline form of the compound of formula I.

* * * * *